United States Patent
Huber et al.

(10) Patent No.: US 9,221,058 B2
(45) Date of Patent: Dec. 29, 2015

(54) DETERMINING THE FINENESS OF A GROUND MATERIAL, IN PARTICULAR AN ORE, IN A MILL

(75) Inventors: Christoph Huber, München (DE); Günter Lugert, München (DE); Randolf Mock, Hohenbrunn (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 474 days.

(21) Appl. No.: 13/820,966

(22) PCT Filed: Aug. 17, 2011

(86) PCT No.: PCT/EP2011/064131
§ 371 (c)(1),
(2), (4) Date: Mar. 5, 2013

(87) PCT Pub. No.: WO2012/034808
PCT Pub. Date: Mar. 22, 2012

(65) Prior Publication Data
US 2013/0166237 A1    Jun. 27, 2013

(30) Foreign Application Priority Data

Sep. 14, 2010   (DE) .......................... 10 2010 040 724

(51) Int. Cl.
*G06F 19/00* (2011.01)
*B02C 17/18* (2006.01)
(Continued)

(52) U.S. Cl.
CPC ............. *B02C 17/1805* (2013.01); *B02C 17/24* (2013.01); *B02C 25/00* (2013.01); *G01N 27/002* (2013.01); *G01N 29/14* (2013.01); *G01N 29/46* (2013.01); *G01N 2291/02458* (2013.01)

(58) Field of Classification Search
CPC .. B22F 3/004; B22F 2202/05; G03G 9/08755
USPC ..................................... 702/64, 66, 182–185
See application file for complete search history.

(56) References Cited

U.S. PATENT DOCUMENTS

| 4,722,485 A | 2/1988 | Young et al. ............. B02C 17/18 |
| 5,360,174 A | 11/1994 | Persson ................... B02C 17/20 |

(Continued)

FOREIGN PATENT DOCUMENTS

| DE | 3527293 A1 | 2/1987 | ............. B02C 17/18 |
| JP | 55165207 A | 12/1980 | ............. B21B 25/00 |

(Continued)

OTHER PUBLICATIONS

Chilean Office Action, Application No. 480-13, 6 pages, Jun. 15, 2015.

(Continued)

*Primary Examiner* — Edward Raymond
(74) *Attorney, Agent, or Firm* — Slayden Grubert Beard PLLC (57) ABSTRACT

Methods and arrangements for determining the fineness of a ground material in a mill are provided, wherein the acoustic spectrum of the mill during the grinding process is used for concluding the fineness. The mill comprises a drum in which the ground material is present during the grinding process, said drum being driven by a magnetic drive having at least one magnetic segment during the grinding process, so that a rotating magnetic field generated with the aid of the magnetic drive causes the drum to rotate. In order to determine the acoustic spectrum, a voltage induced in a coil of the magnetic segment is determined at least intermittently. On the basis of a model, using the detected time-dependent induced voltage, conclusions can be drawn about the acoustic spectrum and therefrom about the fineness.

20 Claims, 3 Drawing Sheets (51) Int. Cl.
*G01N 27/00* (2006.01)
*B02C 17/24* (2006.01)
*B02C 25/00* (2006.01)
*G01N 29/14* (2006.01)
*G01N 29/46* (2006.01)

(56) References Cited

U.S. PATENT DOCUMENTS

| | | | | |
|---|---|---|---|---|
| 6,820,829 B1 * | 11/2004 | Oder | ................. | B02C 15/04 |
| | | | | 241/119 |
| 6,874,364 B1 | 4/2005 | Campbell et al. | ....... | B02C 17/18 |
| 7,845,583 B2 | 12/2010 | Svedberg et al. | ............... | 241/30 |
| 2005/0279870 A1 | 12/2005 | Scuccato | ................. | B02C 17/24 |

FOREIGN PATENT DOCUMENTS

| | | | | |
|---|---|---|---|---|
| RU | 2412005 C2 | 2/2011 | ................. | B02C 7/14 |
| SU | 869809 A1 | 10/1981 | ............. | B02C 25/00 |
| WO | 2007/094711 A1 | 8/2007 | ................ | B02C 7/14 |
| WO | 2012/034808 A1 | 3/2012 | ............. | B02C 17/18 |

OTHER PUBLICATIONS

International Search Report and Written Opinion, International Application No. PCT/EP2011/064131, 22 pages, Dec. 5, 2011.

* cited by examiner

DETERMINING THE FINENESS OF A GROUND MATERIAL, IN PARTICULAR AN ORE, IN A MILL

CROSS-REFERENCE TO RELATED APPLICATIONS

This application is a U.S. National Stage Application of International Application No. PCT/EP2011/064131 filed Aug. 17, 2011, which designates the United States of America, and claims priority to DE Patent Application No. 10 2010 040 724.0 filed Sep. 14, 2010. The contents of which are hereby incorporated by reference in their entirety.

TECHNICAL FIELD

The present disclosure relates to methods and arrangements for determining the fineness of a ground material, for example, an ore, in a mill.

BACKGROUND

Ores are today ground in the immediate vicinity of their extraction site and pressed into pellets so they can be transported as economically as possible and optimally preprocessed especially for the smelting process. The grinding process is extremely energy-intensive, with ore extraction and (pre)processing now accounting for approximately 1.4% of global annual energy demand. Preprocessing ores as energy-efficiently as possible is accordingly highly significant in terms of protecting the climate and using resources sparingly.

With typical electric power ratings for driving mills in the range of approximately 20 MW it is very important to control the grinding process such that on the one hand the ground material's properties will conform to the specifications stipulated for pelleting. On the other hand, for energy efficiency reasons the grinding process must not last longer than is necessary to meet said specifications. That requires a sensor system which on the one hand will make a meaningful measured variable available for assessing the fineness. The ground material's fineness is therein defined substantially by the shape of the individual ore fragments, in particular by their diameter or, as the case may be, the spectrum of their size distribution. On the other hand the sensor system needs to be sufficiently robust to operate reliably in the extremely adverse environment because extremely high downtime costs will result from an outage of such a system.

Methods for determining the fineness are known in the case of which the acoustic spectrum or what is termed the "acoustic fingerprint" of the mill's drum during the grinding process is determined. Conclusions about the shape of the ground material can be drawn from the spectrum so that, based on the spectrum's evaluation, a decision can be made as to whether the required fineness has been attained. Proven techniques for determining the spectrum are measuring by means of acceleration sensors secured directly to the drum, and using microphones directed at places on the drum's outer skin that emit particularly characteristic frequency data.

However, measuring the acoustic spectrum with the aid of acceleration sensors poses the problem of how to convey the signals from the drum site to a central unit that evaluates the measured signals. That can scarcely be done with adequate reliability by applying classical electrical solutions, for example using ring grinders. While a cableless sensor system such as, for instance, the industrial variant of the WLAN protocol would have better realization prospects, the problem with that is how to make the necessary electric energy available to the system robustly and on a permanent basis.

When the acoustic fingerprint is recorded via suitably positioned microphones, conveying the structure-borne sound from the drum to the microphones via the air constitutes a loss path which may in some circumstances seriously falsify important acoustic information or, as the case may be, not convey it with sufficient quality. In the extremely dusty and otherwise dirty environment it is furthermore doubtful whether microphones are able to meet the requirements placed on stability and robustness.

SUMMARY

One embodiment provides a method for determining the fineness of a material being ground in a mill, with the mill having a drum in which the material being ground is located during the grinding process and which during the grinding process is driven by a magnetic drive, having at least one magnetic segment, through the drum's being made to rotate by a rotating magnetic field generated with the aid of the magnetic drive, wherein a voltage induced in a coil of the magnetic segment is determined at least intermittently and conclusions are drawn about the fineness from the induced voltage that was determined.

In a further embodiment, the acoustic spectrum of the drum is first ascertained from the induced voltage that was determined and conclusions about the fineness are drawn from the acoustic spectrum.

In a further embodiment, the acoustic spectrum is determined from the fineness on the basis of a model.

In a further embodiment, the induced voltage will only be determined if the relationship $V_I = I_B/I_{B,max}$ between the momentary current $I_B$ flowing in the magnetic segment for generating the magnetic field and the maximum current $I_B/max$ flowing in the coil for generating the rotating magnetic field is within a prespecified range of $V_I \in [a_I; b_I]$, e.g., a range of $V_I \in [-5\%; +5\%]$, e.g., a range of $V_I \in [-2\%; +2\%]$.

In a further embodiment, the induced voltage will only be determined if the relationship $V_U = U_B/U_{B,max}$ between the voltage $U_B$ momentarily being applied in the magnetic segment for generating the magnetic field and the maximum voltage $U_{B,max}$ being applied in the coil for generating the rotating magnetic field is within a range of $V_U \in [a_U; b_U]$, e.g., a range of $V_U \in [-5\%; +5\%]$, e.g., a range of $V_U \in [-2\%; +2\%]$.

In a further embodiment, the induced voltage will only be determined if the momentary current $I_B$ flowing in the magnetic segment for generating the magnetic field exhibits substantially the value zero.

In a further embodiment, the coil is a coil serving to generate the rotating magnetic field.

In a further embodiment, the voltage induced in the coil is a mutual-induction voltage due to a temporal change in the magnetic flux in an air gap between the drum and magnetic segment.

In a further embodiment, the temporal change within the air gap is due to vibrations in the drum, with the acoustic frequency spectrum of the vibrations depending on the fineness, in particular being reproducibly determined by the fineness.

In a further embodiment, the magnetic drive has a plurality of magnetic segments (131/i, where i=1, 2, 3) distributed around the circumference of the drum, with the voltage induced in a coil (133/i, where i=1, 2, 3) of the respective magnetic segment being determined individually for each of the magnetic segments and conclusions about the fineness being drawn from the induced voltage that was determined.

In a further embodiment, the individual induced voltages are determined periodically cycling round the circumference of the drum or simultaneously by using a plurality of the magnetic segments.

Another embodiment provides an arrangement for determining the fineness of a material being ground in a mill, with the mill having a drum in which the material being ground is located during the grinding process and which during the grinding process can be driven by a magnetic drive, having at least one magnetic segment, through the drum's being made to rotate by a rotating magnetic field generated with the aid of the magnetic drive, wherein a measuring device and a data processing device are provided, with a voltage induced in a coil of the magnetic segment being determined at least intermittently by means of the measuring device and the data processing device being embodied for drawing conclusions about the fineness from the induced voltage that was determined.

In a further embodiment, the measuring device is part of the magnetic segment.

In a further embodiment, the magnetic drive has a plurality of magnetic segments (131/$i$, where i=1, 2, 3) distributed around the circumference of the drum, with the voltage induced in a coil (133/$i$, where i=1, 2, 3) of the respective magnetic segment being measurable individually for each of the magnetic segments and conclusions about the fineness being respectively drawn in the data processing device from said induced voltages that were measured.

In a further embodiment, the data processing device is embodied for calculating an acoustic spectrum of the drum from an induced voltage that was measured.

In a further embodiment, the data processing device is embodied for determining the fineness from the acoustic spectrum in particular on the basis of a model.

BRIEF DESCRIPTION OF THE DRAWINGS

Exemplary embodiments will be explained in more detail below on the basis of the schematic drawings, wherein.

DETAILED DESCRIPTION

Embodiments of the present disclosure provide a robust possibility for determining information about a ground material's fineness during a grinding process.

To determine the drum's acoustic fingerprint and, therefrom, the fineness, certain embodiments make use of the magnetic—particularly electromagnetic—segments employed in the case of mills having an electromagnetic drum drive for driving the drum. Said solution will allow the fineness to be determined both contactlessly and without sensors.

In contrast to certain known approaches that employ dedicated sensor hardware, the acoustic fingerprint is determined by means of the mill's electromagnetic drive coils.

With the disclosed method for determining the fineness of a material being ground in a mill, with the mill having a drum in which the material being ground is located during the grinding process and which during the grinding process is driven by a magnetic drive, having at least one magnetic segment, through the drum's being made to rotate by a rotating magnetic field generated with the aid of the magnetic drive, a voltage induced in a coil of the magnetic segment is determined at least intermittently and conclusions about the fineness are drawn from the induced voltage that was determined.

The drum's acoustic spectrum may be first ascertained from the induced voltage that was determined and conclusions about the fineness are drawn from the acoustic spectrum.

The acoustic spectrum may be determined from the fineness on the basis of a model.

In some embodiments, the induced voltage and hence the acoustic spectrum will only be determined if the relationship $V_I = I_B / I_{B,max}$ between the momentary current $I_B$ flowing in the magnetic segment for generating the magnetic field and the maximum current $I_{B,max}$ flowing in the coil for generating the rotating magnetic field is within a prespecified range of $V_I \in [a_I; b_I]$, e.g., a range of $V_I \in [-5\%; +5\%]$, e.g., a range of $V_I \in [-2\%; +2\%]$.

Alternatively, the induced voltage and hence the acoustic spectrum will only be determined if the relationship $V_U = U_B / U_{B,max}$ between the voltage $U_B$ momentarily being applied in the magnetic segment for generating the magnetic field and the maximum voltage $U_{B,max}$ being applied in the coil for generating the rotating magnetic field is within a range of $V_U \in [a_U; b_U]$, e.g., a range of $V_U \in [-5\%; +5\%]$, e.g., a range of $V_U \in [-2\%; +2\%]$.

In some embodiments, the induced voltage and hence the acoustic spectrum will only be determined if the momentary current $I_B$ flowing in the magnetic segment for generating the magnetic field or, as the case may be, the voltage $U_B$ being applied for generating said current exhibits substantially the value zero.

The coil is a coil serving to generate the rotating magnetic field. Thus there will be no need for additional sensors or other means for recording measured values and use can instead be made of components already present.

The voltage induced in the coil is a mutual-induction voltage due to a temporal change in the magnetic flux in an air gap between the drum and magnetic segment.

The temporal change within the air gap is therein due to vibrations in the drum, with the acoustic frequency spectrum of the vibrations depending on the fineness, in particular being reproducibly determined by the fineness, or, as the case may be, clearly correlating with the acoustic spectrum, being in particular very largely identical down to one factor.

The magnetic drive has a plurality of magnetic segments distributed around the drum's circumference, with the voltage induced in a coil of the respective magnetic segment being determined individually for each of the magnetic segments and conclusions about the fineness being drawn from the induced voltage that was determined.

An individual acoustic spectrum can therefore be determined by means of any of the magnetic segments by measuring a voltage induced in a coil of the respective magnetic segment and deriving the respective acoustic spectrum from the induced voltage that was measured.

The individual induced voltages or, as the case may be, acoustic spectra can be determined
  periodically cycling round the drum's circumference or
  simultaneously by using a plurality of the magnetic segments.

The disclosed arrangement may enable the fineness of a material being ground in a mill to be determined. The mill has a drum in which the material being ground is located during the grinding process and which during the grinding process can be driven by a magnetic drive, having at least one magnetic segment, through the drum's being made to rotate by a rotating magnetic field generated with the aid of the magnetic drive. A measuring device and a data processing device are provided, with a voltage induced in a coil of the magnetic segment being determined at least intermittently by means of the measuring device and the data processing device being embodied for drawing conclusions about the fineness from the induced voltage that was determined.

The measuring device may be part of the magnetic segment, meaning is integrated in or directly connected to the magnetic segment. In particular the magnetic segment and measuring device form a unit.

The magnetic drive may have a plurality of magnetic segments distributed around the drum's circumference, with the voltage induced in a coil of the respective magnetic segment being individually measurable for each of the magnetic segments and conclusions about the fineness being in each case drawn in the data processing device from said induced voltages that were measured.

The data processing device may be embodied for calculating an acoustic spectrum of the drum from an induced voltage that was measured.

The data processing device may furthermore be embodied for determining the fineness from the acoustic spectrum in particular on the basis of a model.

In some embodiments, therefore, an improved method for determining the fineness of a material being ground in a mill is proposed. The mill has a drum in which the material being ground is located during the grinding process and which during the grinding process is driven by a magnetic drive, having at least one magnetic segment, through the drum's being made to rotate by a rotating magnetic field generated with the aid of the magnetic drive. The drum's acoustic spectrum is determined at least intermittently during the grinding process and conclusions about the fineness are drawn from the acoustic spectrum. A voltage induced in a coil of the magnetic segment is measured for determining the acoustic spectrum and the acoustic spectrum is derived from the induced voltage that was measured.

The noise spectrum requiring to be evaluated is fed substantially from two sources. Noises are on the one hand contained that are produced by the drive and also include natural oscillations induced within the mill's structure. These are periodic and hence deterministic. Said noise component can therefore be quantified on the basis of mechano-acoustic models of the mill and subtracted out using, for example, a model-based filtering process. The other source of noise is the material requiring to be fragmented by the grinding means. Said material has a shape resulting randomly from the cutting process in the quarry or mine. The shapes and sizes of the lumps and fragments of rock are therefore stochastic. The noises produced when they drop down are accordingly also stochastic in character. No temporal correlation exists here between the individual noises. That presents the possibility of separating one component of the noise spectrum from the other component with a high degree of accuracy. The power source is the motor, whose power characteristic over time is known sufficiently accurately. That, though, will also allow the vibrations in the mill's mechanical structure to be formally represented (resonance functions, etc.) and subtracted from the overall spectrum. What will remain is the stochastic component due substantially to the tumbling motion of the rocks and fragments.

Figure 1A:
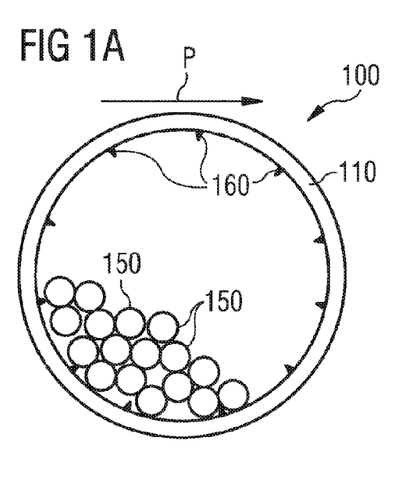
FIGS. 1A-1C show a cross-section through a drum of a mill without any material for grinding and with ground material of different finenesses.
Figure 1B:
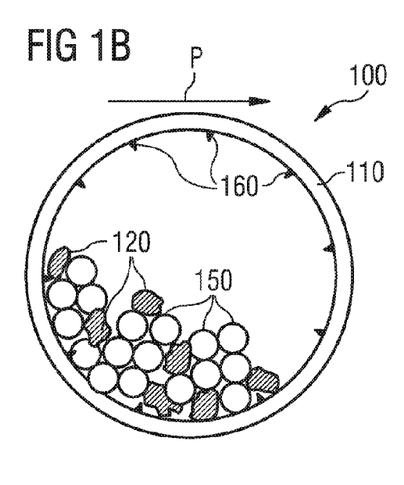
Figure 1C:
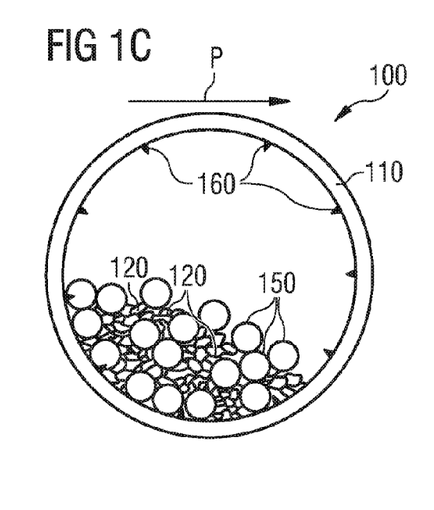
Figure 2A:
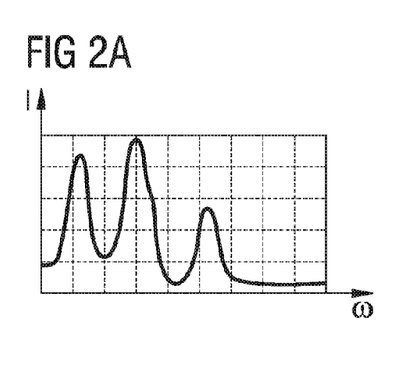
FIGS. 2A-2C show acoustic spectra corresponding to the conditions shown in FIG. 1.
Figure 2B:
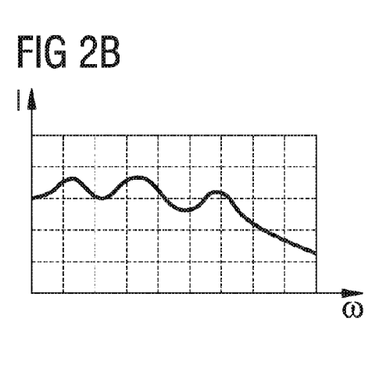
Figure 2C:
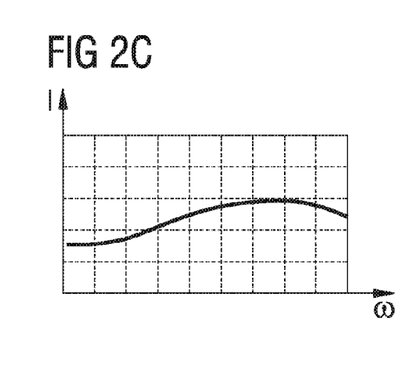

FIGS. 1A to 1C show a cross-section through a drum 110—rotating in the direction of arrow P— of a mill 100, for example an ore ball mill. Drum 110 is shown in FIG. 1A not having any material for grinding; FIGS. 1B and 1C show the drum having ground material 120 exhibiting two different finenesses (for the sake of clarity only some of the material 120 being ground has been labeled with reference numerals in the figures). Shown additionally in FIGS. 2A to 2C are the corresponding acoustic spectra in the form of the sound intensity I ($\omega$) emitted by the drum as a function of the frequency $\omega$. Measuring said spectra will as explained below allow conclusions to be drawn about the fineness.

Figure 3:
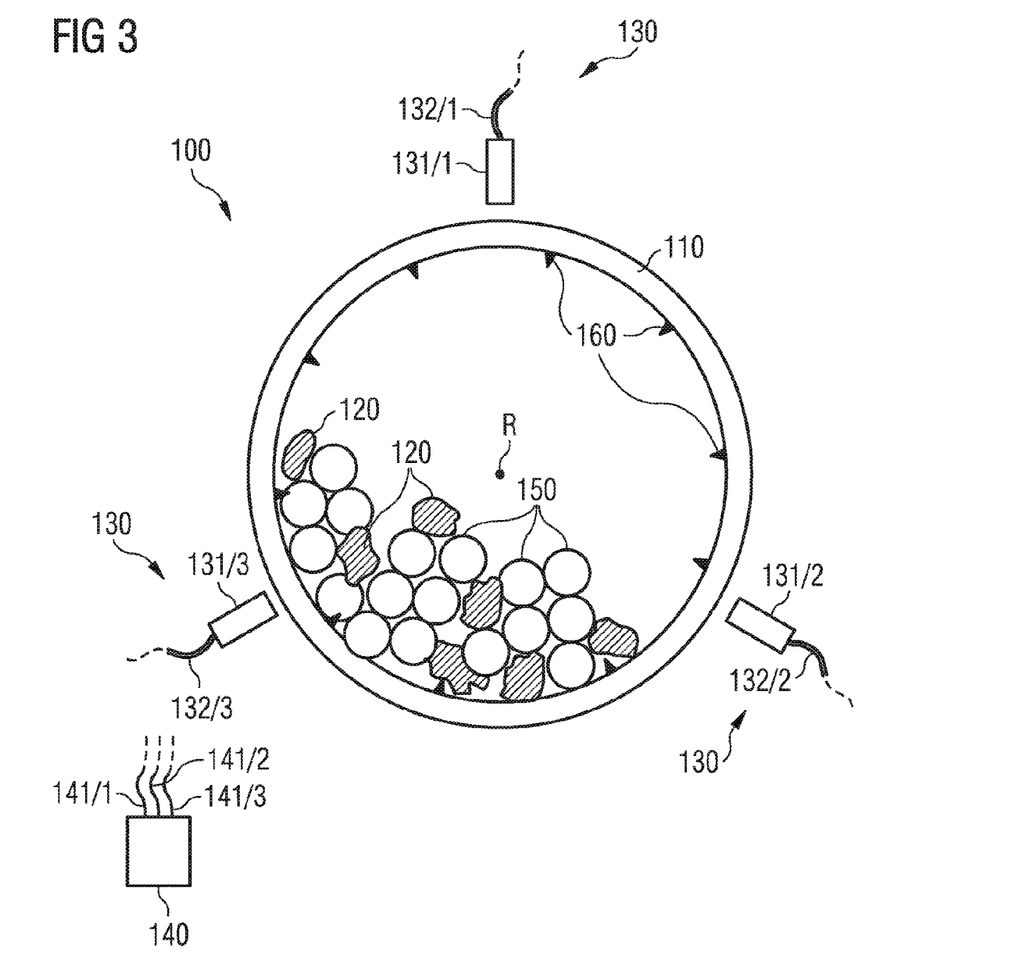
FIG. 3 shows a drum of a mill having a magnetic drive.

In the case of an ore mill 100 employing a gearless electric drive system, drum 110 of mill 100 is made to rotate P not by way of an external motor having a downstream gearing but instead with the aid of a drive 130 which, as shown in simplified form in FIG. 3, has a plurality of electromagnetic segments 131/1, 131/2, 131/3 (or, as the case may be, 131/$i$ where i=1, 2, 3). Said segments are controlled via cable connections 132/$i$, 141/$i$ by corresponding power electronics 140 in such a way as to produce a magnetic field whose orientation rotates around the axis R of drum 110 at a constant angular velocity. Drum 110 mounted at both its ends will likewise be made to rotate by said rotating magnetic field and the corresponding magnetic forces. The magnetic field's rotational speed and hence also the speed at which drum 110 rotates can be varied by electrically controlling the drive or, as the case may be, electromagnetic segments 131/$i$ appropriately.

In order now to grind the material 120 requiring to be ground or, as the case may be, the ore 120 in the exemplary embodiment explained here, drum 110 of ball mill 100 is first filled with a grinding means 150, namely with steel balls 150 in the case of the ball mill (for the sake of clarity only some of balls 150 have been labeled with reference numerals in the figures). Said balls have, at least when new, very largely identical diameters. When drum 110 is made to rotate, balls 150 are to a certain extent compliantly moved by carriers 160 located in drum 110 until they drop from carrier 160 and hit the floor of drum 110 (again, for the sake of clarity only some of carriers 160 have been labeled with reference numerals in the figures).

What is induced in the mechanical structure of drum 110 owing to the considerable masses being moved therein is an acoustic noise spectrum I ($\omega$) that is generated on the one hand by drive 130 itself along with its mechanical components, but on the other hand by balls 150 being compliantly moved and then dropping again. Owing to the uniform size of the balls and the low attenuation present, an acoustic spectrum I ($\omega$) can be expected to result that exhibits characteristic resonance structures and in which not only a mechanical structure of mill 100 or drum 110 but also the geometry and mass of balls 150 are expressed in the form of characteristic frequencies. A corresponding spectrum I ($\omega$) of a drum 110 filled only with balls 150 and containing no material requiring to be ground is shown schematically in FIG. 2A.

If a material 120 requiring to be ground, for example freshly extracted ore, is then put into drum 110, the acoustic spectrum I ($\omega$) that can be measured while drum 110 is rotating will change substantially. Owing to their irregularly shaped surfaces and the widely scattered size distributions of the lumps 120 of ore as well as the greatly increased friction due to their surface structure, the resonances of the spectrum can be expected to appear significantly overdamped and hence broader and weaker in intensity. The result is a broad acoustic continuum that falls away toward higher frequencies $\omega$. This can be seen in FIG. 2B.

Ore 120 will be present in the form of fine grains once the desired fineness has been attained. A relatively high-frequency tumbling noise can then be measured while drum 110 is rotating. The now small grains of ore will moreover produce a strong attenuation so that no or scarcely any more resonances will occur in the acoustic spectrum I ($\omega$). What can instead be expected is a continuum of the frequency-dependent acoustic intensity I ($\omega$) having a maximum at higher frequencies (FIG. 2C).

Determining the acoustic spectrum will accordingly allow conclusions to be drawn about the fineness.

Figure 4:
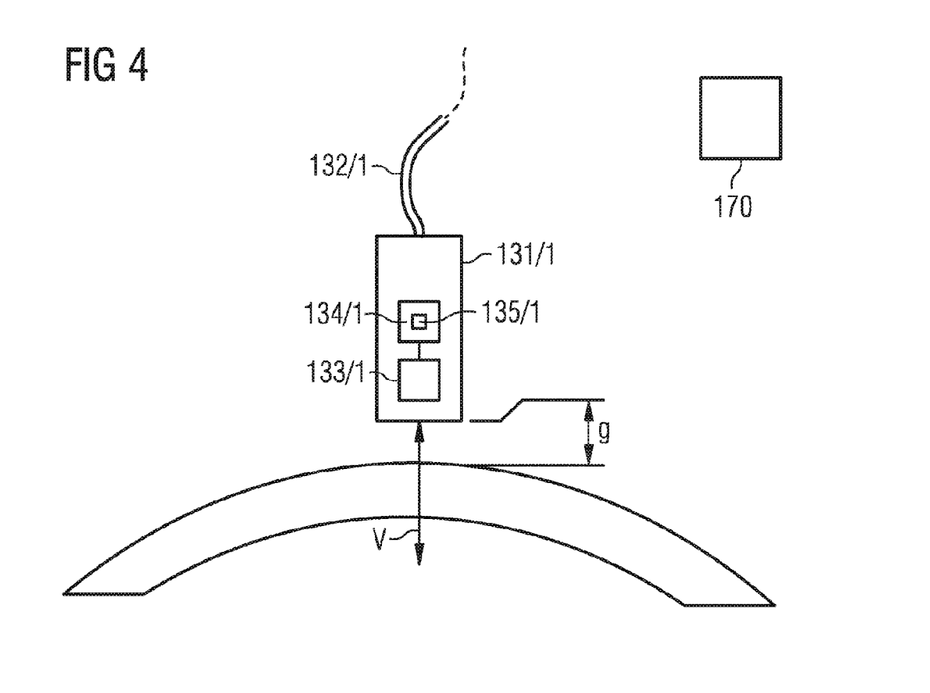
FIG. 4 shows a magnetic segment.

FIG. 4 shows a section of drum 110 as well as the magnetic segment 131/1 from drive arrangement 130 of electromagnets 131. The field generated by electromagnet 131/1 produces a magnetic flux $\Phi$ in the air gap g between magnetic segment 131/1 and drum 110. If vibrations V are then induced in drum 110 owing to the grinding process, they will give rise to a temporal change within air gap g:

$$g(t) = g_0 + \sum_i A_i \cdot \sin(\omega_i t - \varphi_i) \qquad \text{Eq. 1}$$

Eq. 1 describes the temporal change within air gap g through a spectrum of acoustic excitations containing the frequencies $\omega_i$ and respective phase shifts $\varphi_i$.

The temporal change in the air gap g(t) results in a change in magnetic flux $\Phi$ across gap g so that according to Lenz's rule a voltage $U_{ind}$ acting counter to said change in flux will be induced in coil 133/1 of magnetic segment 131/1:

$$U_{ind} = -\frac{d\Phi}{dt} = -\frac{\partial \Phi}{\partial g}\frac{dg}{dt} = -\frac{\partial \Phi}{\partial g} \cdot \sum_i A_i \cdot \omega_i \cdot \cos(\omega_i t - \varphi_i) \qquad \text{Eq. 2}$$

It was therein initially assumed that the change in flux for small geometric changes in air gap g behaves approximately linearly with g, and Eq. 1 was then used.

Eq. 2 shows that temporally modulating air gap g between a magnetic segment 131/1 and drum 110 of ore mill 100 will result in an induction voltage $U_{ind}$ that changes over time in coil 133/1 of magnetic segment 131/1 and which contains the information about frequency spectrum I ($\omega$) with which the drum is excited owing to the grinding process. Because $U_{ind}$ behaves proportionally to the derivation over time of the excitation spectrum showing the time dependency on g(t), the various frequency components are weighted with the factor $\omega$. High frequencies will hence tend to have a stronger impact than low frequencies.

An evaluation of mutual-induction component $U_{ind}$ represented by Eq. 2 in the terminal voltage of magnetic coil segment 131/1 will accordingly supply the information about the vibration excitations of drum 110. It is therefore possible to obtain the desired information about the fineness of ore 120 from that voltage component. For example the spectrum I ($\omega$) can be obtained from the time-dependent signal $U_{ind}(t)$ with the aid of a Fourier analysis. Likewise conceivable is a combination with an evaluation that is synchronous with the rotation speed and by means of which the drive components, which are typically periodic in nature, can be suppressed if need be. Ensuing determining of the fineness from the spectrum can be based on a model.

An arrangement for determining the fineness therefore has a measuring device 134/1 with the aid of which induced voltage $U_{ind}$ is measured. Measuring device 134/1 is for that purpose connected to the terminal clips of magnetic coil segment 131/1 or, as the case may be, coil 133/1. Voltage $U_{ind}$ induced in coil 133/1 induces a sensory current flow $I_{ind}$ that can be measured via, for example, a shunt resistor 135/1 belonging to measuring device 134/1. Measuring device 134/1 is connected to a data processing device 170 in which the corresponding spectrum I ($\omega$) is calculated using the Fourier analysis from the induced voltage that was measured.

Measuring device 34/1 can basically be part of the assigned magnetic segment 131/1. The measuring device and assigned magnetic segment can alternatively also be located separately from each other. For example it is conceivable for the measuring device to be accommodated in data processing device 170.

The other magnetic segments 131/2, 131/3 shown in FIG. 3 are analogous thereto in structure. Corresponding measuring devices 134/2, 134/3 are likewise connected to data processing device 170 and possibly accommodated therein.

A particular embodiment of the approach, however, may be used for high-power drives 130 that provide a driving power of several tens of MW. Back-electromotive-force components $U_{ind}$ induced according to Eq. 2 are relatively small in the case of drives of such kind compared with the respective maximum voltage level $U_{B,max}$ and current level $I_{B,max}$ of a coil segment 131, which can be in the kV and kA range. The momentary voltage and current signal $U_B$, $I_B$ by means of which a coil segment 131 is controlled can moreover have not inconsiderable superimposed interference signals. This will make the sensory signal according to Eq. 2 more difficult to evaluate.

Figure 5:
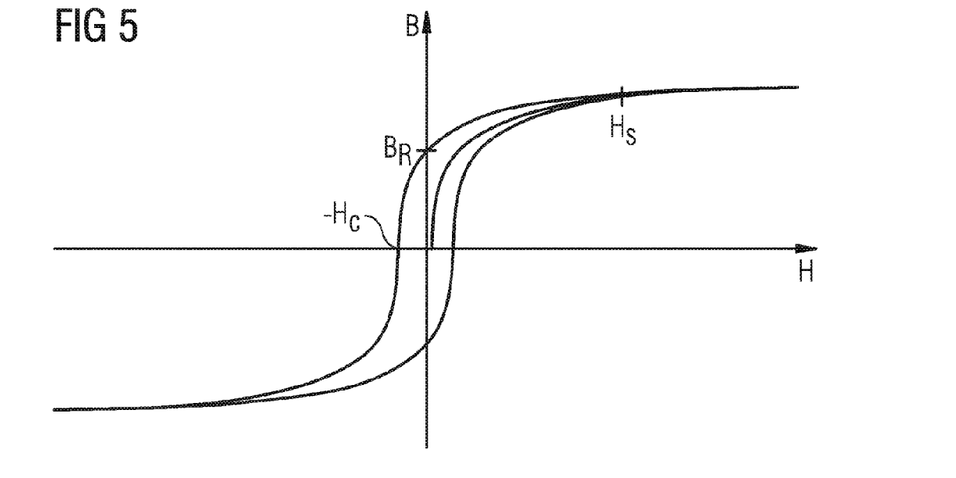
FIG. 5 shows a hysteresis curve.

A special situation will, though, result if the current $I_B$ flowing in a coil segment 131 or, as the case may be, in coil 133 of magnetic coil segment 131 attains the value zero. While it is true that the magnetic field will at that instant be H=0, coil segment 131 and drum 110 will nonetheless exhibit a remanent magnetic induction $B_R$. This is illustrated in FIG. 5 by means of a magnetic hysteresis curve. A remanent magnetic induction $B_R$ occurs in soft magnetic materials when H=0. Said induction can be used as explained below because in the arrangement according to FIG. 4 a magnetic flux $\phi$ will still be present despite there being no current flow in coil 133 of magnetic segment 131 so that in that situation according to Eq. 2 a back electromotive force $U_{ind}$ will be induced that will consequently induce a sensory current flow in the arrangement. Said flow can be measured via, for example, a shunt resistor.

For determining the acoustic spectrum, voltage $U_{ind}$ is therefore ascertained ideally at an instant when the current $I_B$ momentarily flowing in coil 133 of magnetic segment 131 for generating the magnetic field attains the value zero, which is to say when $I_B(t_0)=0$. Measuring at precisely the instant at which $I_B(t_0)=0$ is difficult to realize because the drum carries on rotating. It is, however, also sufficient and practicable for the voltage $U_{ind}$ to be ascertained not just at said instant to but over a period of time $\Delta t$ during which, for example, the relationship $V_I = V_B/I_{B,max}$ between the momentarily flowing current $I_B$ and the maximum current $I_{B,max}$ used for generating the rotating magnetic field is in a range of, for instance, $V_I \in [a; b]$, where a can be −2% and b +2%, for example. The values of parameters a, b will of course affect the accuracy of the measurement. The precise range or, as the case may be, the exact limits a, b of the interval would need to be ascertained individually and experimentally. What is decisive is that the coil voltage present at the relevant instant or, as the case may be, during the relevant period of time is not orders of magnitude higher than the measuring signal.

A comparable interval can of course also be established with the aid of voltages $U_B$, $U_{B,max}$, with its being necessary here, too, to establish the precise limits of the interval individually and experimentally.

It must basically be assumed that a strong current flow will have a much more disruptive effect on the signal evaluation than a high voltage as it may be possible to filter out the latter better.

The induced voltage $U_{ind}$ can in a first embodiment therein actually be measured only at the instants $t_0$ or, as the case may be, during the periods of time $\Delta t$. The induced voltage is in an alternative embodiment measured continuously but is evaluated only at instant $t_0$ or, as the case may be, during the period of time $\Delta t$ in data processing device 170. The expression "measuring the voltage $U_{ind}$" is accordingly not used here but, instead, the expression "determining the voltage $U_{ind}$", which encompasses both said embodiment options.

The reliability of the information obtained in this way about the fineness can be even further improved by providing a sensory evaluation of such kind according to Eq. 2 not just for one of magnetic segments 131/1 but for all or at least several of magnetic segments 131/i of magnetic drive 130. Each of relevant magnetic segments 131/i would accordingly have one of the above-explained measuring devices 134/i that convey the respectively measured induced voltages $U_{ind,i}$ to data processing device 170. The acoustic spectrum will then be ascertained individually for each measuring device in data processing device 170, with the fineness being determined therein from said spectrum and, where applicable, machine components being eliminated by means of an evaluation that is synchronous with the rotation speed.

The individual induced voltages $U_{ind,i}$ may be measured in a periodically cycling manner. To generate the rotating magnetic field by means of a plurality of magnetic segments 131/1, 131/2, 131/3, which as shown in FIG. 3 are arranged around the circumference of drum 110, each of the magnetic segments 131/i cycles through a state in which current $I_B$, i becomes zero, with the cycle duration depending on the magnetic field's rotational speed. The current $I_{B,i}$ is therein not zero in all magnetic segments 131/i simultaneously. Rather it is the case that in the simplest embodiment it is as though the location of magnetic segment 131/i to whose current it has to apply that $I_{B,i}=0$ revolves around the drum at the magnetic field's rotational speed. In other words $I_{B,1}(t1)=0$ applies to current $I_{B,1}$ for example first at an instant t1 in magnetic segment 131/1, then, at an instant t2>t1, $I_{B,2}(t2)=0$ in magnetic segment 131/2, and finally, at instant t3>t2, $I_{B,3}(t3)=0$ in magnetic segment 131/3. The cycle then starts anew, meaning that what again applies at instant t4>t3 is that $I_{B,1}(t4)=0$ in magnetic segment 131/1 etc. Voltage $U_{ind,i}$ is accordingly measured cyclically around the drum's circumference because, for the above-cited reasons, measuring ideally always only takes place when $I_{B,i}=0$ applies in corresponding magnetic segment 131/i.

It is of course also conceivable for measuring to be performed using all segments 131/i simultaneously, with its having to be noted, though, that a measurement of voltage $U_{ind,i}$ can be impaired owing to the very high currents or, as the case may be, voltages that may be present.

The robustness of this measuring method as compared with measuring performed on just one coil can be considerably increased by way of correlating evaluating methods in the case of which correlating with the rotation speed takes place and also with the electric power drive of the drum or of other components of the ore mill, about which components detailed information is likewise available concerning, for example, driving or the movement path, and which methods link together the acoustic information obtained in that way in data processing device 170 (possibly using suitable physical models of the mill's acoustic excitation during different phases of the grinding process).

What is claimed is:

1. A method for determining the fineness of a material being ground in a mill, comprising:
    grinding the material in a drum of the mill,
    using a magnetic drive having a magnetic segment to generate a rotating magnetic field to drive the drum during the grinding process, and,
    at least intermittently determining a voltage induced in a coil of the magnetic segment, and
    determining the fineness of the material based on the determined induced voltage.

2. The method of claim 1, comprising:
    determining an acoustic spectrum of the drum based on the determined induced voltage, and
    determining the fineness of the material based on the determined acoustic spectrum.

3. The method of claim 2, comprising using a model to determine fineness of the material based on the acoustic spectrum.

4. The method of claim 1, comprising determining the induced voltage only if the relationship $V_I=I_B/I_{B,max}$ between the momentary current $I_B$ flowing in the magnetic segment for generating the magnetic field and the maximum current $I_{B,max}$ flowing in the coil for generating the rotating magnetic field is within a prespecified range of $V_I \in [a_I; b_I]$.

5. The method of claim 4, comprising determining the induced voltage only if the momentary current $I_B$ flowing in the magnetic segment for generating the magnetic field exhibits substantially the value zero.

6. The method of claim 1, comprising determining the induced voltage only if the relationship $V_U=U_B/U_{B,max}$ between the voltage $U_B$ momentarily being applied in the magnetic segment for generating the magnetic field and the maximum voltage $U_{B,max}$ being applied in the coil for generating the rotating magnetic field is within a range of $V_U \in [a_U; b_U]$.

7. The method of claim 1, wherein the coil is a coil serving to generate the rotating magnetic field.

8. The method of claim 1, wherein the voltage induced in the coil is a mutual-induction voltage due to a temporal change in the magnetic flux in an air gap between the drum and magnetic segment.

9. The method of claim 8, wherein the temporal change within the air gap is due to vibrations in the drum, with the acoustic frequency spectrum of the vibrations depending on the fineness.

10. The method of claim 1, wherein the magnetic drive has a plurality of magnetic segments distributed around the circumference of the drum,
    wherein the voltage induced in a coil of the respective magnetic segment is determined individually for each of the magnetic segments and conclusions about the fineness are drawn from the induced voltage that was determined.

11. The method of claim 10, wherein the individual induced voltages are determined either:
    periodically cycling round the circumference of the drum, or
    simultaneously by using a plurality of the magnetic segment.

12. The method of claim 1, comprising determining the induced voltage only if the relationship $V_I=I_B/I_{B,max}$ between the momentary current $I_B$ flowing in the magnetic segment for generating the magnetic field and the maximum current $I_{B,max}$ flowing in the coil for generating the rotating magnetic field is within a prespecified range of $V_I \in [-5\%; +5\%]$.

13. The method of claim 1, comprising determining the induced voltage only if the relationship $V_I = I_B/I_{B,max}$ between the momentary current $I_B$ flowing in the magnetic segment for generating the magnetic field and the maximum current $I_{B,max}$ flowing in the coil for generating the rotating magnetic field is within a prespecified range of $V_I \in [-2\%; +2\%]$.

14. The method of claim 1, comprising determining the induced voltage only if the relationship $V_U = U_B/U_{B,max}$ between the voltage $U_B$ momentarily being applied in the magnetic segment for generating the magnetic field and the maximum voltage $U_{B,max}$ being applied in the coil for generating the rotating magnetic field is within a range of $V_U \in [-5\%; +5\%]$.

15. The method of claim 1, comprising determining the induced voltage only if the relationship $V_U = U_B/U_{B,max}$ between the voltage $U_B$ momentarily being applied in the magnetic segment for generating the magnetic field and the maximum voltage $U_{B,max}$ being applied in the coil for generating the rotating magnetic field is within a range of $V_U \in [-2\%; +2\%]$.

16. An arrangement for determining the fineness of a material being ground in a mill having a drum, in which the material being ground is located during the grinding process and which during the grinding process can be driven by a magnetic drive having at least one magnetic segment, the drum being made rotated by a rotating magnetic field generated by the magnetic drive, the arrangement comprising:
a measuring device configured to at least intermittently determine a voltage induced in a coil of the magnetic segment, and
a data processing device configured to determine the fineness of the material based on the determined induced voltage.

17. The arrangement of claim 16, wherein the measuring device is part of the magnetic segment.

18. The arrangement of claim 16, wherein the magnetic drive has a plurality of magnetic segments distributed around the circumference of the drum, wherein the voltage induced in a coil of the respective magnetic segment is measurable individually for each of the magnetic segments and conclusions about the fineness are respectively drawn in the data processing device from said induced voltages that were measured.

19. The arrangement of claim 16, wherein the data processing device is embodied for calculating an acoustic spectrum of the drum from an induced voltage that was measured.

20. The arrangement of claim 19, wherein the data processing device is embodied for determining the fineness from the acoustic spectrum based on a model.

* * * * *